United States Patent
Smits et al.

(10) Patent No.: US 6,343,230 B1
(45) Date of Patent: Jan. 29, 2002

(54) HEARING EVALUATION DEVICE WITH PREDICTIVE CAPABILITIES

(75) Inventors: Matthijs P. Smits, Woodside; Christophe M. Coppin, Carlsbad, both of CA (US)

(73) Assignee: Natus Medical, Inc., San Carlos, CA (US)

( * ) Notice: Subject to any disclaimer, the term of this patent is extended or adjusted under 35 U.S.C. 154(b) by 0 days.

(21) Appl. No.: 09/479,557

(22) Filed: Jan. 7, 2000

(51) Int. Cl.$^7$ ................................................ A61B 5/04
(52) U.S. Cl. ........................................ 600/544; 600/559
(58) Field of Search ................................. 600/544, 545, 600/547, 559

(56) References Cited

U.S. PATENT DOCUMENTS

| | | | | |
|---|---|---|---|---|
| 4,275,744 A | * | 6/1981 | Thornton et al. | 600/599 |
| 4,493,327 A | * | 1/1985 | Bergelson et al. | 600/544 |
| 4,545,388 A | * | 10/1985 | John | 600/544 |
| 5,003,986 A | * | 4/1991 | Finitzo et al. | 600/544 |
| 5,230,344 A | * | 7/1993 | Ozdamar et al. | 600/544 |
| 5,601,091 A | * | 2/1997 | Dolphin | 600/559 |
| 5,697,379 A | * | 12/1997 | Neely et al. | 600/544 |
| 5,916,174 A | * | 6/1999 | Dolphin | 600/559 |
| 5,999,856 A | * | 12/1999 | Kennedy | 607/57 |
| 6,071,246 A | * | 6/2000 | Sturzebecher et al. | 600/559 |
| 6,080,112 A | * | 6/2000 | Don | 600/559 |

\* cited by examiner

*Primary Examiner*—Robert L. Nasser
*Assistant Examiner*—Navin Natnithithadha
(74) *Attorney, Agent, or Firm*—Orrick, Herrington & Sutcliffe LLP (57) ABSTRACT

An apparatus and method for evaluation of hearing loss is disclosed. The apparatus and method use evoked Auditory Brainstem Responses (ABR) to determine if the subject is able to hear repeatedly administered click stimuli. In order to expedite evaluation, the present invention uses normative data to accurately predict when a subject is likely to fail the test, so that evaluation will not needlessly continue for a subject who is very unlikely to pass.

27 Claims, 4 Drawing Sheets

HEARING EVALUATION DEVICE WITH PREDICTIVE CAPABILITIES

RELATED APPLICATIONS

This application is related to the co-pending and commonly assigned U.S. Patent Application entitled "Hearing Evaluation Device with Patient Connection Evaluation Capabilities," Ser. No. 09/479,559 filed by Matthijs P. Smits, Vineet Bansal, Abraham J. Totah and Bryan P. Flaherty and the U.S. Patent Application entitled "Hearing Evaluation with Noise Detection and Evaluation Capability," Ser. No. 09/479,548 filed by Matthijs P. Smits and Bryan P. Flaherty, the disclosures of which are hereby incorporated herein by reference.

FIELD OF THE INVENTION

The present invention relates to devices and methods that use electroencephalographic responses to auditory stimuli to evaluate the hearing of a subject, and that are capable of quickly and accurately determining when a subject is unlikely to pass the hearing loss test.

BACKGROUND OF THE INVENTION

In the past, hearing impairment in babies and children was often not detected until after it was observed that the baby or child did not respond normally to sound. Unfortunately, it often took months or even years for the parent to observe the impairment, and by that time the child's language and learning abilities were negatively and often irreversibly impacted. Indeed, recent studies indicate that the vocabulary skills of hearing impaired children markedly increases if their hearing loss is detected early. The optimal time to evaluate hearing loss is thus immediately after birth, both because early detection allows for early treatment, and because parents often fail to bring their infants to later appointments. As a result, a number of states have implemented programs to evaluate newborns for hearing loss.

However, babies, especially newborns, cannot participate in traditional hearing tests, which require the subject to indicate if he or she hears the auditory stimulus. Thus, devices and methods have been developed to objectively determine hearing loss, without the voluntary participation of the subject. One such method involves analysis of the involuntary electroencephalographic (EEG) signals that are evoked from a subject in response to an auditory stimulus. It has been found that when a subject is able to perceive a sound having particular characteristics, a specific EEG waveform known as an Auditory Brainstem Response (ABR) is generated. This ABR response signal is typically small in magnitude in relation to general EEG activity. Therefore, statistical and signal processing techniques have been employed and developed to help detect, to a predefined level of statistical confidence, whether an ABR response has in fact been evoked. ABR testing is especially applicable to evaluation of infants, but can be applied to any subject.

The ABR that is evoked in response to the auditory stimulus may be measured by use of surface electrodes on the scalp or neck. As a practical matter, the electrodes will also detect noise signals from neural activity (besides the ABR), muscle activity, and non-physiological environmental noises.

Especially for subjects who do not pass the hearing evaluation, ABR testing can be time consuming. It has been found that in many cases a subject's failure to pass can be adequately predicted after a short period of time. This information can be conveyed to the test operator, who may then decide whether to continue with a full length test or not.

The present invention represents a major advance in the art because it allows for early and accurate prediction in many cases that a subject will not pass the evaluation. The resultant time savings may not only allow for more tests per unit time, but may also make such tests more attractive to parents and health care providers.

DESCRIPTION OF THE PRIOR ART

Under prior art, a subject will "pass" the evaluation as soon as enough data have been collected to conclude, within a statistical level of confidence, that an ABR waveform is in fact present. If the data are insufficient to make this conclusion, then the evaluation continues until the total number of individual response signals—known as "sweeps"—exceeds a preset threshold. Prior art devices have sed a threshold of 15,000 sweeps. If testing concludes because the number of sweeps equals the maximum, then the subject would typically be referred for further testing to determine if in fact he or she suffers from hearing impairment.

Given the special difficulties in hearing evaluation of infants, it is important to minimize the time required to conduct a hearing evaluation. It is also important to minimize the time required for evaluation given the goal of universal evaluation. However, under the prior art, a non-hearing subject would need to undergo an entire, full length evaluation session, regardless of whether the data were ambiguous, or whether they showed that it was very unlikely that the subject would pass. Full-length evaluations may last as long as an hour.

OBJECTS AND SUMMARY OF THE INVENTION

The present invention provides a device and method for use in analyzing the EEG signal evoked in response to the auditory click stimulus, to determine if the subject suffers from hearing loss. Broadly, the invention is directed to devices and methods that are capable of predicting a failure to pass a hearing evaluation, based upon an analysis with normative data, and using certain statistical techniques.

In one embodiment of the invention, evoked EEG responses to auditory stimuli are collected, and organized into "sweeps," with each sweep containing the response signal for one auditory stimulus. The sweeps are organized into B blocks, with each block b containing a number of sweeps $N_b$.

The response signal for each sweep is digitized and converted into a series of binary numbers corresponding to whether the amplitude of the response signal is positive or negative at various points in time. The digitized, binary waveform is compared to a benchmark ABR waveform to determine if the ABR is present. To make this determination, a polarity sum is calculated, which represents the sum of the polarities of the response signals within all blocks at each measured point in time. Statistical techniques are then used to determine if an ABR is present, relying upon the expected distribution of polarity sums in the absence of an ABR. This expected distribution is developed theoretically. A "Pass" is triggered if the observed polarity distribution, as represented in a specifically defined test statistic, indicates that the likelihood that an ABR is present is above a predetermined threshold. After a certain number of blocks have been completed, evaluation will cease if a "Pass" has yet not been triggered. Under such circumstances, the subject will be referred for further testing to determine if he or she in fact does suffer from hearing loss.

In accordance with the present invention, the polarity distribution for each block is evaluated independently, and compared with normative data for a hearing subject. These normative data reflect the expected polarity distribution for a hearing subject, given certain testing conditions. In particular, the normative data account for the prevailing noise conditions.

If the average difference between the expected and the observed polarity distributions for all blocks is too great, a "predicted refer" indication is given. The operator may then continue testing (knowing that a predicted refer has been generated), or may terminate the evaluation. The present invention therefore improves upon the prior art because it provides an accurate way to predict a failure to pass, therefore conserving evaluation times and resources, without significantly sacrificing evaluation accuracy.

Although the embodiments described here are directed towards evaluation of newborn hearing, it is believed that the present invention can be applied to any evaluation, whether of hearing or not, in which evoked potentials are analyzed.

As described below, the present invention makes extensive use of normative data. These normative data were derived from analysis of clinical data, and from computer simulations representing different testing conditions. Normative data have been used to develop drawings described in the subsequent paragraph, and are thus representative of clinical and statistical (computer simulated) data that could be compiled by a person of ordinary skill in the art.

BRIEF DESCRIPTION OF THE DRAWINGS

Further features, elements, and advantages of the present invention will become apparent to a person of ordinary skill in the art in view of the following detailed description of a preferred embodiment of the present invention, made with reference to the drawings annexed, in which like reference characters correspond to like elements, and in which.

DESCRIPTION OF THE PREFERRED EMBODIMENT a. Overview

The invention disclosed herein detects, processes and analyzes the EEG response of a subject to certain sound stimuli. A click sound stimulus is repetitively applied to the subject's ear through a transducer. The click stimuli may be applied to one ear at a time (monoaurally), or to both ears simultaneously (binaurally). In a preferred embodiment, monoaural stimuli are applied at 37 Hz.

The EEG response is detected from surface electrodes. Testing may be performed to ensure that the electrodes have been properly placed, and that nothing is impeding the electrodes' ability to detect the EEG response signal. (See U.S. Patent Application entitled "Hearing Evaluation Device With Patient Connection Evaluation Capabilities").

Figure 3:
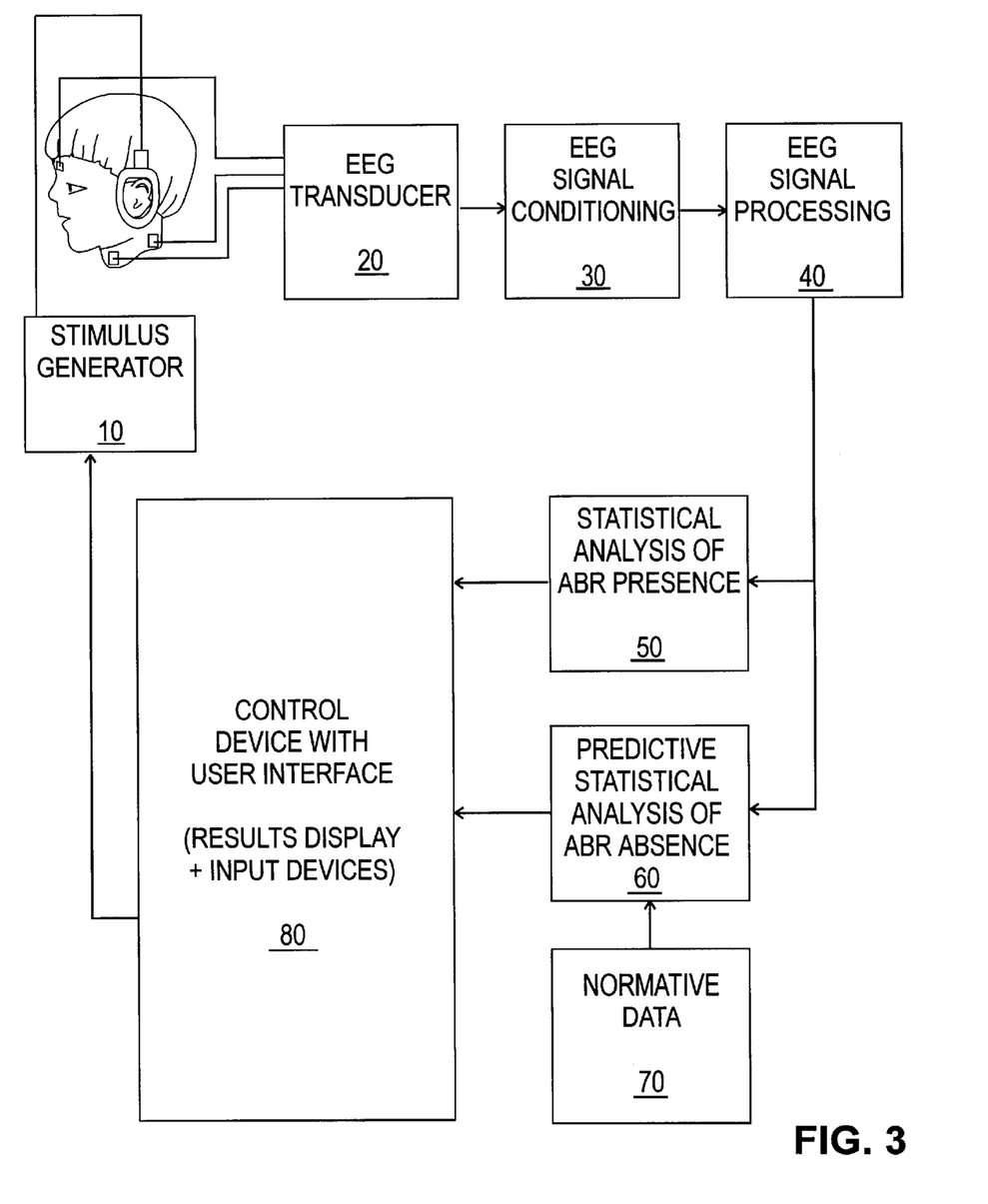
FIG. 3 is a block diagram of the components of the testing apparatus of the present invention.

In a preferred embodiment, the electrodes are placed on the subject in the following manner: a positive electrode is placed on the forehead, a negative electrode is placed on the nape of the neck, and a ground electrode is placed on the mastoid or shoulder (FIG. 3). The EEG signal detected from these electrodes is filtered so as to exclude signals that are not applicable to the ABR.

The amplitude of the EEG response is digitized, and is assigned a binary value. This binary value represents the amplitude polarity of the waveform, that is, whether the EEG amplitude is positive or negative, at the measured time.

The stimuli and responses are grouped into "sweeps" and "blocks." A sweep is a response waveform to a single click stimulus. A block is a series of sweeps, and in a preferred embodiment, represents 500 accepted click stimulus responses. We refer to "accepted" click stimulus responses, because some sweeps may be rejected due to problems with the testing conditions.

Upon completion of a block of accepted sweeps, signal averaging is used to compute the composite waveform that results from this block. In addition, signal averaging is also used to compute the average composite waveform from all blocks combined. This average composite waveform is then compared with an internal template, to determine if the null hypothesis ($H_0$) can be rejected. The null hypothesis is the hypothesis that the baby is hearing-impaired, and will be rejected if the probability of an ABR being present is above a certain pre-set statistical threshold. In the preferred embodiment, the null hypothesis is rejected, and the evaluation ceases, when sufficient data have been collected to conclude, with 99.96% statistical confidence, that an ABR waveform is present. A "Pass" or other similar message may then be generated.

If the average composite waveform is insufficient to reject the null hypothesis, then the evaluation continues until the total number of sweeps exceeds a preset threshold. In addition, for each block, the composite waveform is compared with the same internal template. The resultant comparison value is evaluated against the expected comparison value, based on the test conditions in the block. The differences between the calculated and expected comparison values (based on normative data) are measured for all blocks. The average value of these differences is determined and compared with a threshold, representing a confidence level that the hearing test will likely produce a "refer" result at the end of the test.

b. Signal Analysis

The chief challenge in using ABR to evaluate hearing loss is the difficulty in detecting the ABR response (if any) from the noise within which it is buried. This noise is typically Gaussian-distributed, with a mean amplitude of zero, and with changing variance.

As stated above, the present invention detects the presence of an ABR by repetitively applying click stimuli in blocks b of $N_b$=500 sweeps. Each click stimulus is comprised of a brief acoustic pulse primarily composed of frequencies in the 500–4000 Hz range. The repetition rate for the clicks is 37 Hz. The polarities of the click stimuli are sequentially alternated between condensation (positive square pulse) and rarefaction (negative square pulse) stimuli. Since the noise has a mean of zero and no component is synchronous with the stimulus repetition rates, it is likely to sum toward zero with increasing sweeps, leaving the ABR.

Under the preferred embodiment of the present invention, the amplitude sequence of each click stimulus response is converted into a sequence of polarities (positive or negative) which, in turn, is summed with the other response polarity sequences in block b, to form the array $X_b$. For instance, an amplitude sample in the click stimulus response would be given a "1" if this amplitude were positive (no matter how high), and a "0" if this amplitude were negative (no matter how low). And, if no ABR were present the expected proportion of polarities, which is the same as the polarities of the ABR waveform would be 0.5. However, if an ABR were present, the proportion would likely be higher. The proportion of polarities in an evoked response matching the ABR waveform is related to the amount of signal noise.

After each block of sweeps, the summed polarity sequence $X_b$ for block b is summed with the other summed polarity sequences into an array X. Also, the total number of sweeps N is calculated as the sum of the number of sweeps in each block:

$$\begin{cases} X = \sum_{b=1}^{B} X_b \\ N = \sum_{b=1}^{B} N_b \quad b = 1, 2, \ldots, B \end{cases}$$

Figure 1:
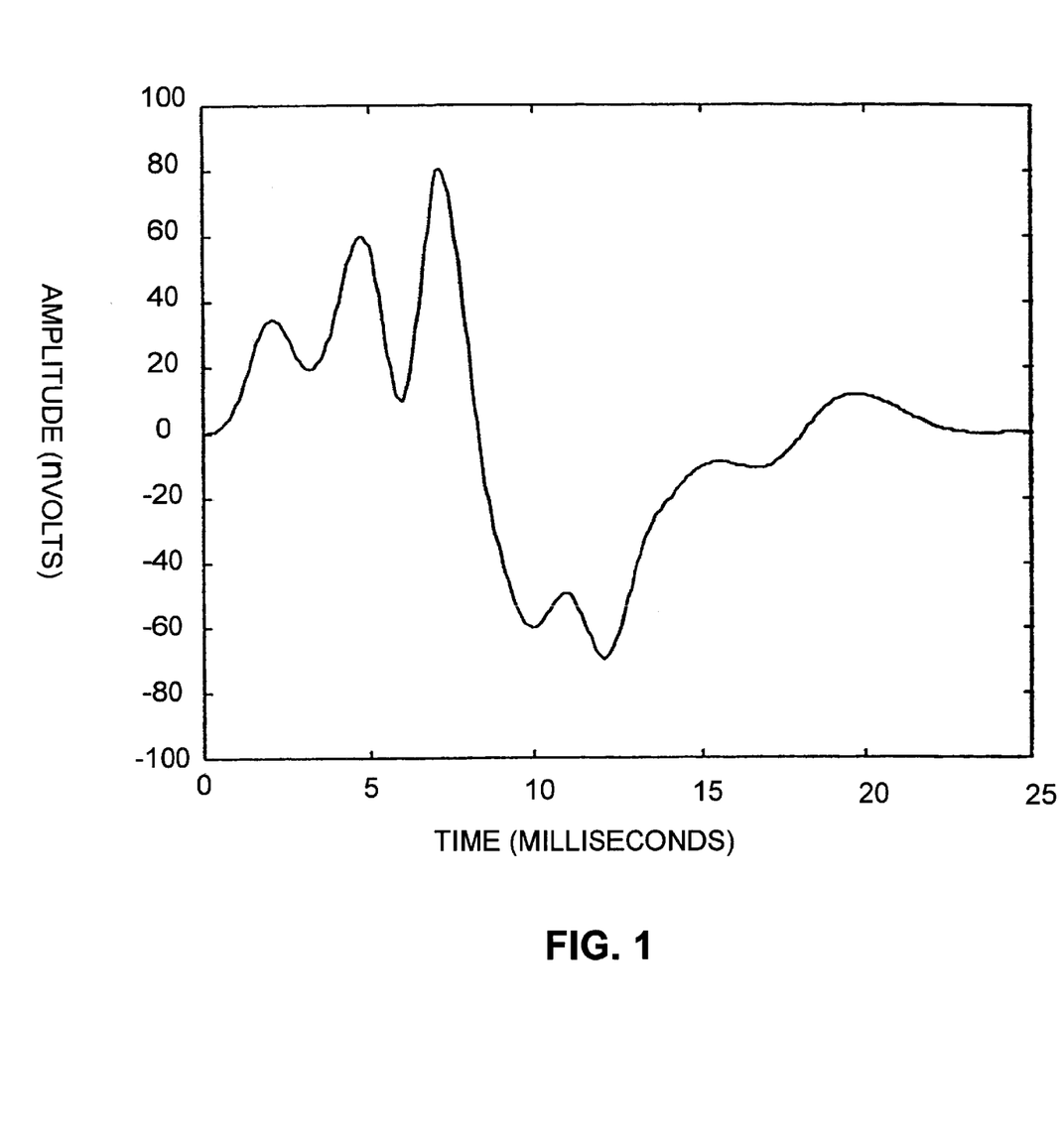
FIG. 1 illustrates a typical ABR waveform.
Figure 2:
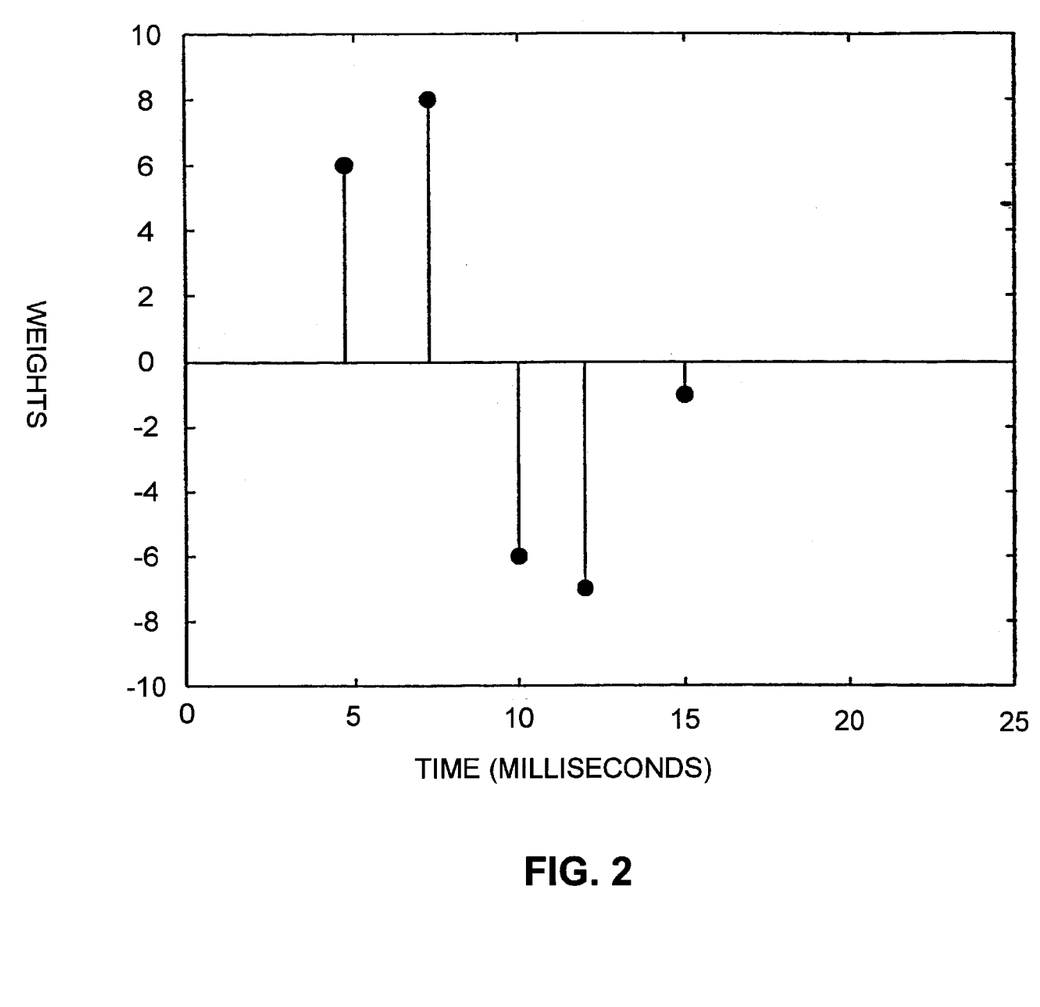
FIG. 2 illustrates a weighted ABR template.

The summed polarity sequence X is then compared with a template waveform, which has been compiled with the use of normative data (FIG. 1). It will be necessary to use different template ABR waveforms for different subject populations and for different hardware configurations. The template waveform is comprised of M weighted points, strategically placed to match the typical ABR waveform. At each of the M points, a weight is assigned, reflecting the importance and polarity of the given measurement point in ascertaining the presence of an ABR, as derived from normative data. (See FIG. 2). The importance of each measurement point is a function of its amplitude. For any given point m, the sum of the polarities would be $x_m$. The sum of the weights equals zero.

The present invention uses a test statistic z to aid in determining if an ABR is present. This test statistic is defined as:

$$z = \frac{\sum_{m=1}^{M} w_m(x_m - \mu_x)}{\sqrt{Npq \sum_{m=1}^{M} w_m^2}}$$

where N is the number of sweeps, p is the probability of positive polarity, and q is the complementary probability. The test statistic z scores the random binary array X by multiplying its elements $x_m$ at each template point m with the corresponding weight $w_m$, and summing these results into a single, normalized number. Now, in the absence of an ABR, the peak of the distribution of z would remain at zero, while in the presence of an ABR, the test statistic would grow with increasing number of sweeps N.

Subjects exhibit variability in the latency of the ABR waveform, so that different subjects, each of whom can hear, may exhibit ABR waveforms at different times after the click stimulus. In order to compensate for this variability, the test statistic z may be recalculated at various times. The highest z from each of these time-shifted samples, $z_{max}$, can be saved and used to determine the presence of the ABR. In a preferred embodiment of the present invention, a "Pass" is indicated when $z_{max}$ reaches a value that is 4 standard deviations from zero.

Additionally, it has been found that the peak-to-peak amplitude of the ABR in normal-hearing babies varies from baby to baby. As explained below, the present invention accounts for this variability in ABR amplitude, by making conservative assumptions about the ABR amplitude of the subject, who is being tested.

The present invention also discloses a method and apparatus for predicting a failure to pass. This is achieved by the statistical methods described below.

Figure 4:
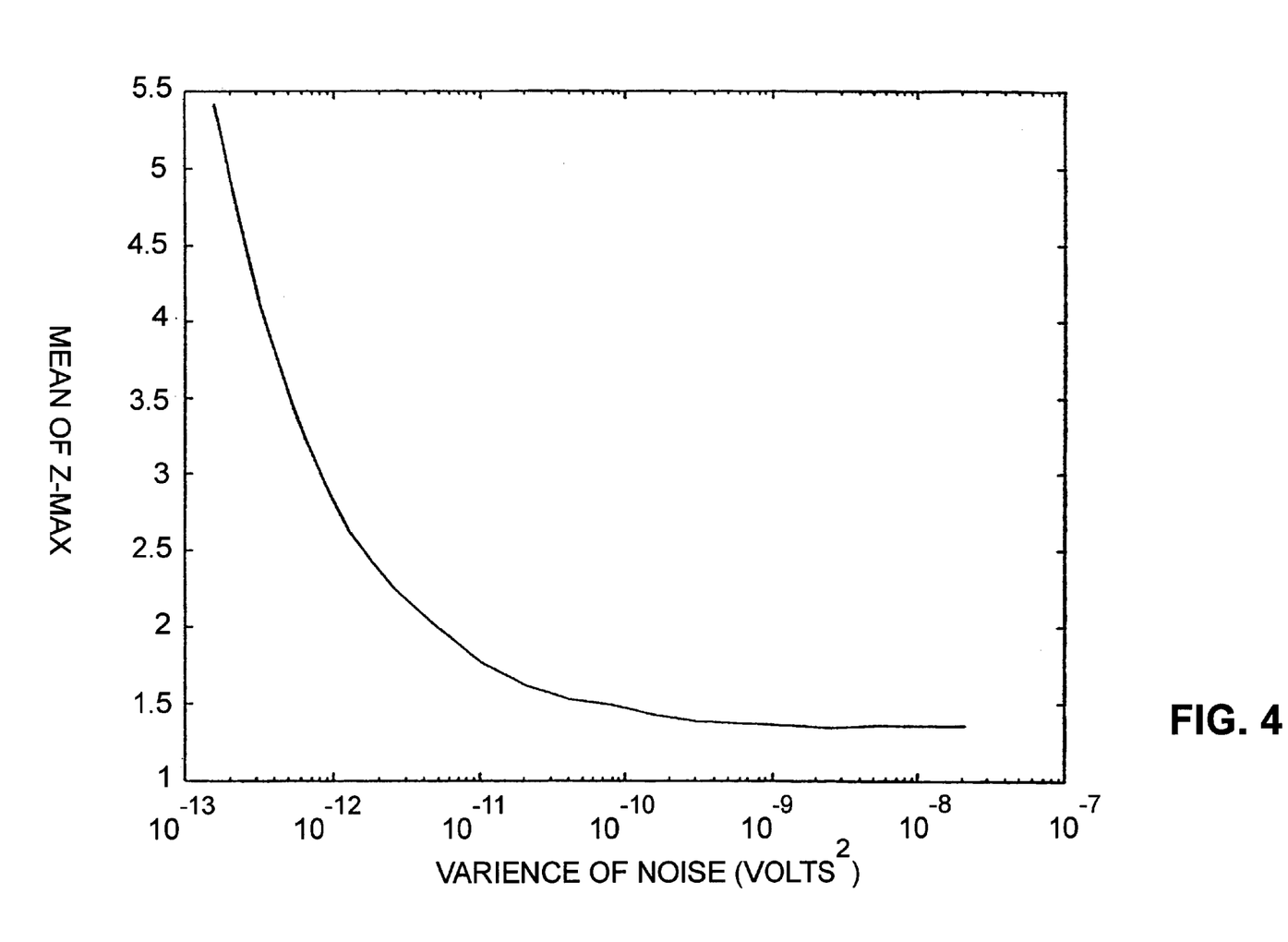
FIG. 4 illustrates the mean of $z_{max}$ as a function of noise variance for a $10^{th}$ percentile ABR waveform.

For each block, the statistic $z_{max}$ and the noise variance $\sigma^2_b$, are calculated. Using normative data, and based on the assumption of a small ($10^{th}$ percentile) ABR waveform, an expected or mean $\mu z_{maxb}$ is derived. In deriving this expected $\mu z_{maxb}$, the present invention takes into the account the EEG signal variance. It has been found that the EEG signal variance affects $z_{max}$ (see FIG. 4), and therefore it is important to take this relationship into account in determining the expected $z_{max}$, based upon the smallest ABR. In particular, tests with normative data indicate that with decreasing EEG signal variance the mean of the test statistic $z_{max}$ grows at increased rates, but the standard deviation of $z_{max}$ remains approximately constant ($\sigma z_{max}$=0.65).

The predicted refer evaluation relies on an analysis of the difference between the expected and actual $z_{max}$. For any given block, $z_{max}$ can be written as:

$$z_{maxb} = \mu_{z_{maxb}} + y_b \sigma_{z_{maxb}} \quad b=1,2,\ldots,B$$

where $\mu_{zmaxb}$ and $\sigma_{zmaxb}$ represent the mean and standard deviation of $z_{maxb}$, and $y_b$ represent a distance factor from the mean. It has been found that the standard deviation of $z_{maxb}$ is approximately constant, and therefore $\sigma_{zmax}$ approximately equals $\sigma_{zmaxb}$. Therefore, the preceding equation can be transformed into:

$$y_b = \frac{z_{\max_b} - \mu_{z_{\max_b}}}{\sigma_{z_{\max}}} \quad b = 1, 2, \ldots, B$$

The probability density function of $y_b$ is a standard normal distribution, representing a normalized distance measure of the outcomes of $z_{maxb}$ from their respective means.

Using this information, the present invention implements a threshold for the triggering of a predicted refer, as follows:

$$\mu_{y_b} = \frac{1}{B} \sum_{b=1}^{B} y_b < y_{threshold} \quad b = 1, 2, \ldots, B$$

In a preferred embodiment, the present invention uses a $\mu_{yb}$ threshold of −1.3, which provides for a 90% confidence level. This threshold level is set so that only the subjects with the 10% lowest $z_{max}$ values for the $10^{th}$ percentile ABR will trigger a predicted refer. Also, rather than automatically terminating the evaluation, in accordance with the present invention the operator may be notified that a predicted refer has been triggered. Using the same principle, the operator may also be notified of the current likelihood that the subject would pass. The operator could then be given the choice of deciding whether to continue with the evaluation or not. In the preferred embodiment, the operator would continue with the test, so that if the subject does not ultimately pass the test, the operator can feel confident that the failure to pass was not caused by exogenous factors.

Also in a preferred embodiment, the predicted refer evaluation is only conducted after the completion of each block, starting at 12 blocks of sweeps.

If the electrodes are improperly placed, the ABR waveform may be inverted, and $z_{max}$ would grow in the opposite direction as the number of sweeps increases. This could falsely trigger a predicted refer, so predicted refer analysis is also conducted using an inverted polarity condition ($\mu_z^{inv} =_{-\bar{x}}$), where $z_{maxb}$ is replaced with the inverse of $z_{maxb}$, and the threshold for a predicted refer is restated as:

$$\mu_{y_b}^{inv} = \frac{1}{B}\sum_{b=1}^{B} y_b^{inv} < y_{threshold} \quad b = 1, 2, \ldots, B$$

With predicted refer analysis conducted for both $z_{max}$ and the inverse of $z_{max}$, the operator can determine if a predicted refer is triggered even if the electrodes are switched. If electrode reversal is detected, the operator may be notified, or the inverted data can be analyzed as if it were not inverted. (ee U.S. Patent Application entitled "Hearing Evaluation Device with Patient Connection Evaluation Capabilities").

These techniques can be used to detect adverse evaluation conditions, such as device errors or noise conditions that erroneously cause the test statistic $z_{max}$ to grow excessively quickly. For example the test could be stopped and the user alerted if $u_y$ exceeded a preset threshold. This threshold could represent the largest $u_y$ expected for the (i.e. the maximum amplitude ABR) based on normative data.

Additionally, failure to pass can also be predicted using standard regression techniques. Extrapolating from the current and previous $z_{max}$ values, one can determine how many sweeps will likely be necessary before $z_{max}$ reaches the threshold value required to generate a "pass." If that number of sweeps exceeds the maximum, then a predicted refer can be generated.

Moreover, the present invention can also be used with different test statistics using other types of signal parameters. For instance, test statistics have been used which employ the ratio between the estimated variance of the averaged total signal and the estimated variance of the background noise. See C. Elberling and M. Don, Quality Estimation of Averaged Auditory Brainstem Responses, Scand. Audiol. 13: 187–197 (1984). It is believed that the prediction techniques described above could be used in conjunction with this test statistic, as well as other test statistics using different signal parameters.

The generation of the click stimulus, the detection of the EEG response signal, the processing and analysis of the EEG response signal including the predicted refer function, and the display of the results are performed by conventional electronic means, e.g., digital microprocessor controlled devices. Such devices include a transducer to generate the auditory stimulus, and conventional electrodes to detect the EEG response signal. To analyze the EEG response signal a processing unit, such a conventional microprocessor, and memory unit are needed. Additionally, a display unit and optionally an input device, such as a mouse and/or a keyboard, provide operator interface.

As shown in FIG. 3, stimulus generator 10 generates the click stimulus, and EEG transducer 20 detects the EEG response to the stimulus. Next, EEG signal conditioning 30 and signal processing 40 occur, readying the EEG response for analysis. Statistical analysis for the presence of an ABR 50 then occurs, and predictive statistical analysis for ABR presence 60 simultaneously occurs, in accordance with the present invention. Normative data 70 is used in latter type of analysis. Finally, a control device with user interface 80 displays the results.

One skilled in the art will appreciate that the present invention can be practiced by other than the preferred embodiments, which are presented for purposes of illustration and not of limitation. In addition, the specific parameter values identified are useful or representative parameter values, and other values or ranges of values for these parameters may be used without departing from the spirit and scope of the invention.

We claim:

1. A device for hearing evaluation of a subject comprising:
   means for repeatedly delivering auditory stimuli;
   means for sampling electroencephalographic responses to said stimuli; and
   means for affirmatively determining that no Auditory Brainstem Response ("ABR") waveform is present in said electroencephalographic responses.

2. A system for hearing evaluation of a subject comprising:
   a transducer having an audible click output stimulus;
   an electrode system adapted to detect an electroencephalographic response to said stimulus; and
   a processor, responsive to said electroencephalographic response, having
     means for sampling the electroencephalographic response;
     means for processing the sampled electroencephalographic response; and
     means for affirmatively determining that no ABR waveform is present in said electroencephalographic responses.

3. A device for hearing evaluation of a subject comprising:
   means for repeatedly delivering auditory stimuli;
   means for sampling electroencephalographic responses to said stimuli; and
   means for predicting that no ABR will be detected in said electroncephalographic responses.

4. The device according to claim 3, wherein the means for predicting that no ABR will be detected in said electroncephalographic response comprises:
   means for detecting the presence of an ABR within a predetermined number of electroencephalographic responses; and
   means for determining, with fewer than said predetermined number of electroencephalographic responses, that the probability that an ABR will be detected is statistically low.

5. A system for hearing evaluation of a subject comprising:
   a transducer having an audible click output stimulus;
   an electrode system adapted to detect electroencephalographic responses to said stimulus; and
   a processor, responsive to said electroencephalographic responses, having
     means for sampling said electroencephalographic responses;
     means for processing said sampled electroencephalographic responses; and
     means for predicting that no ABR will be detected after a predetermined number of said electroencephalographic responses.

6. The system according to claim 5, wherein the means for predicting that no ABR will in be detected in said electroencephalographic response comprises:
   means for detecting the presence of an ABR within a predetermined number of electroencephalographic responses; and
   means for determining, with fewer than said predetermined number of electroencephalographic responses, that the probability that an ABR will be detected is statistically low.

7. A method for hearing evaluation of a subject, comprising the steps of:
repeatedly delivering auditory stimuli;
sampling electroencephalographic responses to said stimuli; and
determining that the probability is statistically low that an ABR waveform is present in said electroencephalographic responses.

8. A method for hearing evaluation of a subject, comprising the steps of:
repeatedly delivering auditory stimuli;
sampling electroencephalographic responses to said stimuli; and
predicting that no ABR will be detected in said electroencephalographic responses.

9. A method of evaluation for hearing loss which comprises the steps of:
repeatedly delivering auditory stimuli to a subject;
measuring electroencephalographic responses to said stimuli, said responses having
an amplitude polarity at each point in time;
digitizing said electroencephalographic responses;
transforming said digitized electroencephalographic responses into a series of binary numbers corresponding to the polarity of the amplitude of said electroencephalographic responses;
transforming said binary numbers into an array of polarity sums;
calculating a test statistic $z_{max}$ based upon said array of polarity sums; and
determining the probability that no ABR waveform is present in said electroencephalographic responses by analysis of said test statistic $z_{max}$.

10. The method according to claim 9, wherein the step of determining that no ABR waveform is present in said electroencephalographic responses by analysis of said test statistic $z_{max}$ comprises:
calculating an expected mean value of $z_{max}$;
comparing $z_{max}$ with said expected mean value by using a distance factor; and
determining that the probability that no ABR waveform is present in said electroencephalographic responses is statistically low when the distance factor is below a predetermined threshold.

11. The method according to claim 10, wherein the expected mean value of $z_{max}$ is derived from normative data.

12. The method according to claim 11, further comprising the steps of:
calculating a signal to noise ratio;
taking into account the signal to noise ratio in calculating the expected mean value of $z_{max}$.

13. The method according to claim 12, further comprising providing the predetermined threshold as −1.3.

14. A method of evaluation for hearing loss which comprises the steps of:
repeatedly delivering auditory stimuli to a subject;
measuring electroencephalographic responses to said stimuli, said responses having
an amplitude polarity at each point in time;
digitizing said electroencephalographic responses;
transforming said digitized electroencephalographic responses into a series of binary numbers corresponding to the polarity of the amplitude of said electroencephalographic responses;
transforming said binary numbers into an array of polarity sums;
calculating a test statistic $z_{max}$ based upon said array of polarity sums; and
determining the presence of adverse evaluation conditions by analysis of said test statistic $z_{max}$.

15. The method according to claim 14, wherein the step of determining the presence of adverse evaluation conditions by analysis of said test statistic $z_{max}$ comprises:
calculating an expected mean value of $z_{max}$;
comparing $z_{max}$ with said expected mean value by using a distance factor; and
determining the presence of adverse evaluation conditions when the distance factor is above a predetermined threshold.

16. The method according to claim 15, wherein the expected mean value of $z_{max}$ is derived from normative data.

17. A method of evaluation for hearing loss which comprises the steps of:
repeatedly delivering auditory stimuli to a subject;
measuring electroencephalographic responses to said stimuli, said responses having
an amplitude polarity at each point in time;
digitizing said electroencephalographic responses;
transforming said digitized electroencephalographic responses into a series of binary numbers corresponding to the polarity of the amplitude of said electroencephalographic responses;
transforming said binary numbers into an array of polarity sums;
calculating a test statistic $z_{max}$ based upon said array of polarity sums; and
predicting that no ABR will be detected in said electroencephalographic responses by analysis of the test statistic $z_{max}$.

18. The method according to claim 17, wherein the step of predicting that no ABR will be detected after a predetermined number of electroencephalographic responses by analysis of the test statistic $z_{max}$ comprises:
calculating an expected mean value of $z_{max}$;
comparing $z_{max}$ with its expected mean value by using a distance factor; and
predicting that no ABR will be detected after a predetermined number of electroencephalographic responses when the difference factor is below a predetermined threshold.

19. The method according to claim 18, wherein the expected mean value of $z_{max}$ is derived from normative data.

20. The method according to claim 19, additionally comprising the steps:
calculating a signal to noise ratio;
taking into account the signal to noise ratio in calculating the expected mean value of $z_{max}$.

21. The method according to claim 17, further comprising providing the predetermined threshold as −1.3.

22. A method for detecting an evoked response, comprising the steps of:
delivering stimuli;
sampling responses to said stimuli; and
predicting that said responses do not contain said evoked response.

23. The method according to claim 22, wherein the step of predicting that said responses do not contain said evoked response comprises:

determining the statistical distribution of said responses;

calculating the probability that said statistical distribution would occur given the existence of said evoked response; and comparing said probability to a predetermined threshold.

24. A method for detecting an evoked response, comprising the steps of:

delivering stimuli;

sampling responses to said stimuli; and predicting that said responses contain said evoked response.

25. The method according to claim 24, wherein the step of predicting that said responses contain said evoked response comprises:

determining the statistical distribution of said responses;

calculating the probability that said statistical distribution would occur given the absence of said evoked response; and comparing said probability to a predetermined threshold.

26. A method of evaluation for hearing loss which comprises the steps of:

repeatedly delivering auditory stimuli to a subject;

measuring electroencephalographic responses to said stimuli, said responses having an amplitude polarity at each point in time;

digitizing said electroencephalographic responses;

transforming said digitized electroencephalographic responses into a series of binary numbers corresponding to the polarity of the amplitude of said electroencephalographic responses;

transforming said binary numbers into an array of polarity sums;

calculating a test statistic $z_{max}$ based upon said array of polarity sums; and using regression analysis to determine the probability that no ABR waveform is present in said electroencephalographic response.

27. A method of evaluation for hearing loss which comprises the steps of:

repeatedly delivering auditory stimuli to a subject;

measuring electroencephalographic responses to said stimuli, said responses containing a signal parameter;

digitizing said electroencephalographic responses;

calculating a test statistic based upon said signal parameter; and determining the probability that no ABR waveform is present in said electroencephalographic response by analysis of said test statistic.

* * * * *